KALANCHOE PLANT
Filed Dec. 20, 1974
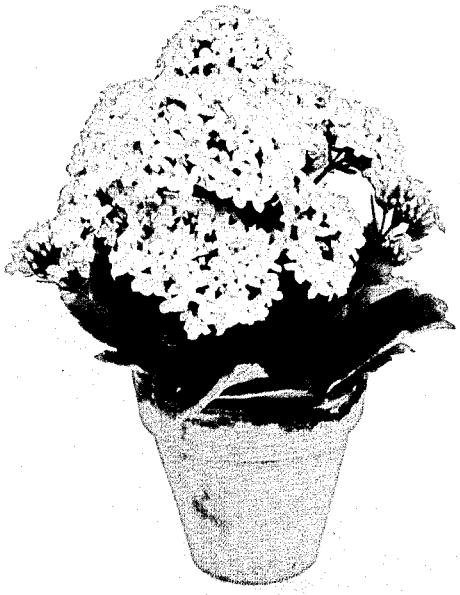

United States Patent

Plant Pat. 3,872

Patented Apr. 27, 1976

3,872

KALANCHOE PLANT

Norbert Bull, Gonnebek, Germany, assignor to Mikkelsens, Inc., Ashtabula, Ohio

Filed Dec. 20, 1974, Ser. No. 535,199

Int. Cl. A01h *5/00*

U.S. Cl. Plt.—68 1 Claim

The present invention relates to a new and distinct variety of Kalanchoe plant known by the varietal name Cherie.

The new variety was discovered by me as a selected, cultivated seedling resulting from a cross between B101, the unnamed seed parent, and B103, the unnamed pollen parent. The new cultivar was asexually reproduced by stem cuttings at Gonnebek, West Germany, and the unique characteristics of the new cultivar have been transmitted through successive propagations.

The new cultivar is particularly characterized by its firm and uniform growth, numerous medium sized umbels on strong stems, with the flowers comprising each umbel being arranged to form a round flower ball; superior blooming habit; distinctive leaf structure, and by its excellent keeping qualities.

The natural blooming season of the new cultivar is mid to late January, although by steered culturing in the greenhouse, the cultivar can be brought to flowering during the entire year. Flowering response, as controlled by the initiation of short day treatment, is 12 weeks in summer and 14–16 weeks in winter. The time from sticking of cuttings to flowering is 20 or 28 weeks for summer and winter, respectively.

The accompanying color photographic drawing shows a typical blooming plant of the new cultivar, with the color being as true as possible with color illustrations of this type.

The following is a detailed description of my new Kalanchoe variety based on plants produced under commercial practices grown in 12 cm. pots maturing in mid July. Color references are made to the Royal Horticultural Society Colour Chart except where general terms of ordinary dictionary significance are used.

PARENTAGE

The new cultivar is a seedling resulting from crossing the seed parent B101, an unnamed and unpatented variety, with the pollen parent B103, also an unnamed and unpatented Kalanchoe variety.

PROPAGATION

Asexually propagates true to type, from stem cuttings.

(A) *Type cutting*: 15 mm. to 25 mm. long terminal cuttings.

(B) *Time to Root*:

12–15 days at 24° C., summer.

18–22 days at 20°, winter.

(C) *Rooting habit*: Typical for commercial cultivars, having a profusion of fibrous denritic roots.

PLANT DESCRIPTION (A) *Form*: Erect, low, compact, and firm. Main stem is vigorous, self supporting, measuring 8 to 10 mm. in diameter. Self branching is pronounced during periods of high light; partially self branching during winter months.

(B) *Habit of growth*: Medium strong for commercial cultivars. Plants become quite full at maturity because of self branching habit or induced brancing by removal of apical bud.

(C) *Foliage description*: Compared to my other Kalanchoe cultivars Granat, Roter Pfeffer, and Korall, disclosed in my pending U.S. appilcations Ser. Nos. 535,200; 535,087 and 535,128, respectively, all of which were filed Dec. 20, 1974, the foliage of Cherie is the least distinctive both in size and form.

(1) *Size*: Small to medium measuring approximately 6 cm. wide to 7–8 cm. long, leaf petiole approximately 10 mm. long.

(2) *Shape*: Beginning somewhat elliptical in early development to nearly oval at maturity.

(3) *Texture*: Upperside, slightly rugose, thick, fleshy, coriaceous; underside, glabrous.

(4) *Margin*: Immature crenate to nearly entire at maturity.

(5) *Color*. Young foliage top side green 137BC; underside between yellow green 147B and 148B; mature foliage top side green 137AB; underside yellow green 147B.

FLOWERING DESCRIPTION (A) *Flowering habits*: Flower development is typically of cylindrical cyme, with total flowering generally over a period of four to six weeks; first flowers are often completely mature before last flowers begin to open; high number of peduncles allows for full show of flowers even though flower development is over relatively long period of time. Plants grown as indicated usually have eight or more primary peduncles each having additional pairs of secondary peduncles creating a massive inflorescence.

(B) *Natural flowering season*: In northern latitudes is mid to late January. Flowering time under controlled day length at 22° C. in summer is 11–12 weeks; in winter is 12–13 weeks. Cherie tends to elongate under high temperatures during summer; such growth can be controlled by using the growth regulator.

(C) *Flower bud description*: Upright, slender measuring 1 mm. to 1.5 mm. in diameter to 4–5 mm. in length before opening. Light red reverse of overlapping petals appear at opening.

(D) *Flowers borne*: On compound paniculate cymes. The primary peduncles measure approximately 12 to 15 cm. long; secondary peduncles measure approximately 6 to 8 cm. long; individual flower pedicels are 2–3 mm. long.

(E) *Quantity of flowers*: Total quantity is quite high for kalanchoes because of the large numbers of primary and secondary flowering shoots. Each cluster of flowers generally has 13–15 individual flowers.

(F) *Petals*:

(1) *Shape*: Nearly elliptical, measuring approximately 4 mm. wide x 8 mm. long; total flower diameter 16–17 mm.

(2) *Color*: In summer, top side, when opening red between 42A and 43A, fading to red 42C toward 41A; underside, red 51CD.

(3) *Number of petals*: Generally four.

(G) *Reproductive organs*:

(1) *Stamens*: Eight in number (a) *Anther shape*: Typical, color medium brown.

(b) *Filament color*: Light green.

(c) *Pollen color*: Yellow.

(2) *Pistils*:

(a) *Stigma shape*: Flat, color crystalline white.

(b) *Style color*: Light yellowish green.

(c) *Ovaries*: Four in number; size, 2–3 mm.; color, green.

DISEASE RESISTANCE

When Cherie has been grown among other Kalanchoe cultivars infected with mildew, it does not become infected.

I claim:

1. A new and distinct variety of Kalanchoe plant characterized particularly by its firm and uniform growth, numerous medium sized umbels on strong stems, with the red flowers comprising each umbel being arranged to form a round flower ball; superior blooming habit, and by its excellent keeping qualities.

No references cited.

ROBERT E. BAGWILL, Primary Examiner